US010180422B1

(12) United States Patent
Sigal

(10) Patent No.: US 10,180,422 B1
(45) Date of Patent: Jan. 15, 2019

(54) METHODS OF TREATING A NEUROENDOCRINE TUMOR

(71) Applicant: Scripps Health, San Diego, CA (US)

(72) Inventor: Darren Sigal, San Diego, CA (US)

(73) Assignee: SCRIPPS HEALTH, San Diego, CA (US)

( * ) Notice: Subject to any disclaimer, the term of this patent is extended or adjusted under 35 U.S.C. 154(b) by 0 days.

(21) Appl. No.: 15/683,630

(22) Filed: Aug. 22, 2017

(51) Int. Cl.
G01N 33/50 (2006.01)
C12Q 1/6886 (2018.01)
G01N 33/574 (2006.01)

(52) U.S. Cl.
CPC ....... *G01N 33/5017* (2013.01); *C12Q 1/6886* (2013.01); *G01N 33/5748* (2013.01); *G01N 33/57446* (2013.01); *C12Q 2600/112* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | |
|---|---|---|
| 7,579,473 B2 | 8/2009 | Bannen et al. |
| 8,030,302 B2 | 10/2011 | Li et al. |
| 8,299,057 B2 | 10/2012 | Lombardi et al. |
| 8,404,846 B2 | 3/2013 | Claridge et al. |
| 8,513,263 B2 | 8/2013 | Haas et al. |
| 8,637,672 B2 | 1/2014 | Flynn et al. |
| 8,785,632 B2 | 7/2014 | Cui et al. |
| 9,187,489 B2 | 11/2015 | Takeda et al. |
| 2015/0073036 A1 | 3/2015 | Hawryluk et al. |
| 2015/0283132 A1 | 10/2015 | Lim et al. |
| 2016/0046639 A1 | 2/2016 | Takeda et al. |
| 2016/0137654 A1 | 5/2016 | Arrigo et al. |

FOREIGN PATENT DOCUMENTS

| | | |
|---|---|---|
| WO | WO-2012139134 A2 | 10/2012 |
| WO | WO-2016061228 A1 | 4/2016 |
| WO | WO-2016196671 A1 | 12/2016 |
| WO | WO-2017106492 A1 | 6/2017 |

OTHER PUBLICATIONS

Amato et al. Chromosome 3p alterations in pancreatic endocrine neoplasia. Virchows Arch 458:39-45 (2011).
Amatu et al. NTRK gene fusions as novel targets of cancer therapy across multiple tumour types. ESMO Open 1(2):e000023 (2016).
Banck et al. The genomic landscape of small intestine neuroendocrine tumors. J Clin Invest 123(6):2502-2508 (2013).
Clinical Trials NCT02568267. Basket Study of Entrectinib (RXDX-101) for the Treatment of Patients With Solid Tumors Harboring NTRK 1/2/3 (Trk A/B/C), ROS1, or ALK Gene Rearrangements (Fusions) (STARTRK-2). (4 pgs.) (Verified Nov. 2016).
Corbo et al. MEN1 in pancreatic endocrine tumors: analysis of gene and protein status in 169 sporadic neoplasms reveals alterations in the vast majority of cases. Endocr Relat Cancer 17:771-783 (2010).
Dong et al. New strategies for advanced neuroendocrine tumors in the era of targeted therapy. Clin Cancer Res 18(7):1830-1836 (2012).
Fernandez-Cuesta et al. Abstract 1531: Cross-entity mutation analysis of lung neuroendocrine tumors sheds light into their molecular origin and identifies new therapeutic targets. Proceedings: AACR Annual Meeting 2014. (2 pgs.) (Apr. 5-9, 2014).
Huang et al. TRK Receptors: Roles in Neuronal Signal Transduction. Annu Rev Biochem 72:609-642 (2003).
Jiao et al. DAXX/ATRX, MEN1, and mTOR pathway genes are frequently altered in pancreatic neuroendocrine tumors. Science 331(6021):1199-1203.
Klimstra et al. The spectrum of neuroendocrine tumors: histologic classification, unique features and areas of overlap. Am Soc Clin Oncol Educ Book 2015:92-103 (2015).
Kulke et al. High-resolution analysis of genetic alterations in small bowel carcinoid tumors reveals areas of recurrent amplification and loss. Gene Chromosomes Cancer 47:591-603 (2008).
Marchetti et al. Frequent mutations in the neurotrophic tyrosine receptor kinase gene family in large cell neuroendocrine carcinoma of the lung. Hum Mutat 29(5):609-616 (2008).
Missiaglia et al. Pancreatic endocrine tumors: expression profiling evidences a role for AKT-mTOR pathway. J Clin Oncol 28(2):245-255 (2010).
Nagano et al. Allelic alterations in pancreatic endocrine tumors identified by genome-wide single nucleotide polymorphism analysis. Endocr Relat Cancer 14:483-492 (2007).
Oberg et al. Genetics and molecular pathology of neuroendocrine gastrointestinal and pancreatic tumors (gastroenteropancreatic neuroendocrine tumors). Curr Opin Endocrinol Diabetes Obes 16(1):72-78 (2009).
Oberg et al. Molecular pathogenesis of neuroendocrine tumors: implications for current and future therapeutic approaches. Clin Cancer Res 19(11):2842-4849 (2013).
Odate et al. TrkB/BDNF signaling pathway is a potential therapeutic target for pulmonary large cell neuroendocrine carcinoma. Lung Cancer 79:205-214 (2013).
Rekhtman et al. Next-Generation Sequencing of Pulmonary Large Cell Neuroendocrine Carcinoma Reveals Small Cell Carcinoma-like and Non-Small Cell Carcinoma-like Subsets. Clin Cancer Res 22(14):3618-3629 (2016).

(Continued)

*Primary Examiner* — Karen A. Canella
(74) *Attorney, Agent, or Firm* — Wilson Sonsini Goodrich & Rosati

(57) ABSTRACT

Disclosed herein, are methods of treating a neuroendocrine tumor (NET) in an individual in need thereof, comprising administering to the individual a therapeutically effective amount of an agent that inhibits a tropomyosin receptor kinase (Trk) protein, wherein the NET is associated with a Trk protein that has undergone a genetic translocation or is an NTRK gene fusion protein. Also disclosed herein are methods of treating a neuroendocrine tumor (NET) in an individual in need thereof, comprising: (a) obtaining a sample of NET genetic material from the individual; (b) determining whether the NET tumor comprises a NTRK translocation or gene fusion; and (c) administering to the individual a therapeutically effective amount of an agent that inhibits a tropomyosin receptor kinase (Trk) protein.

19 Claims, 5 Drawing Sheets

(56) References Cited

OTHER PUBLICATIONS

Russo et al. Acquired Resistance to the TRK Inhibitor Entrectinib in Colorectal Cancer. Cancer Discov 6(1):36-44 (2016).
Tatematsu et al. Investigation of neurotrophic tyrosine kinase receptor 1 fusions and neurotrophic tyrosine kinase receptor family expression in non-small-cell lung cancer and sensitivity to AZD7451 in vitro. Mol Clin Oncol 2:725-730 (2014).
Vaishnavi et al. TRKing down an old oncogene in a new era of targeted therapy. Cancer Discov 5(1):25-34 (2015).
Wang et al. Application of next generation sequencing to human gene fusion detection: computational tools, features and perspectives. Brief Bioninform 14:506-519 (2013).
Xavier et al. Small bowel neuroendocrine tumors: From pathophysiology to clinical approach. World J Gastrointest Pathophysiol 7(1):117-124 (2016).
Yao et al. One hundred years after "carcinoid": epidemiology of and prognostic factors for neuroendocrine tumors in 35,825 cases in the United States. J Clin Oncol 26(18):3063-3072 (2008).
Yeh et al. NTRK3 kinase fusions in Spitz tumours. J Pathol 240(3):282-290 (2016).
Signal, D. et al. Activity of Entrectinib in a Patient With the First Reported NTRK Fusion in Neuroendocrine Cancer. J Natl Compr Canc Netw. Nov. 2017;15(11):1317-1322.
PCT/US2018/047330 Invitation to Pay Additional Fees dated Oct. 24, 2018.
Ricciuti et al. Targeting NTRK fusion in non-small cell lung cancer: rationale and clinical evidence. Med Oncol. 34(6):105 (2017).

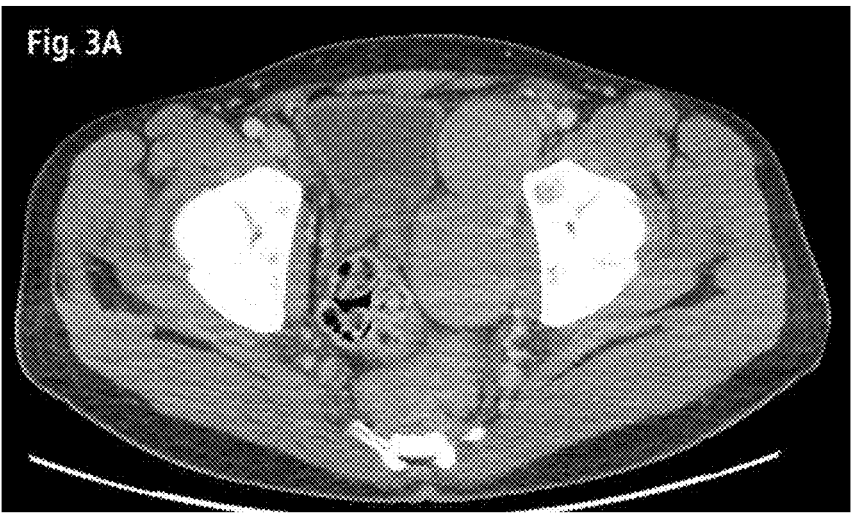
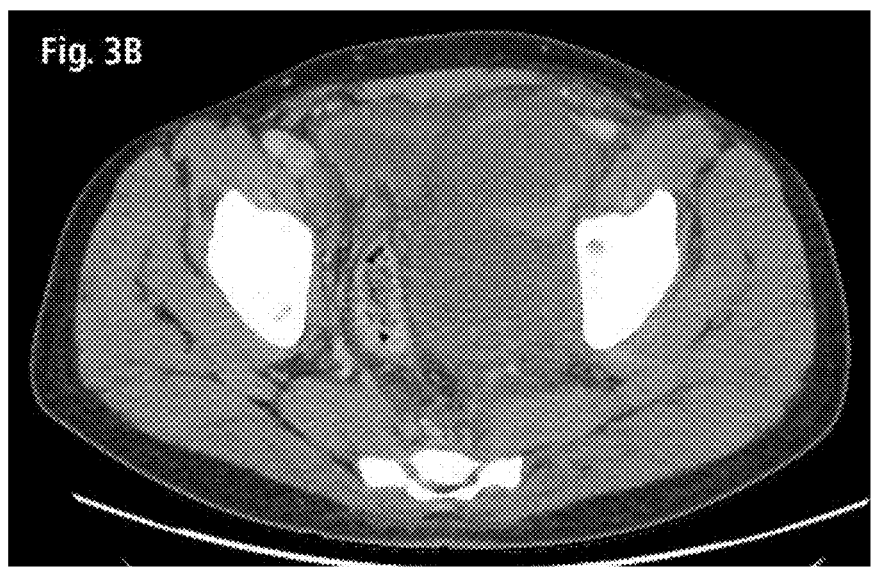

METHODS OF TREATING A NEUROENDOCRINE TUMOR

BACKGROUND OF THE INVENTION

With a median survival of only 33 months, patients with metastatic neuroendocrine tumors (NETs) have a poorer prognosis than previously realized. With a reported five-fold increase in incidence over the past thirty years and a prevalence of 35 per 100,000, the diagnosis and treatment of NETs have become an important unmet medical need.

SUMMARY OF THE INVENTION

Disclosed herein, in some embodiments, are methods of treating a neuroendocrine tumor (NET) in an individual in need thereof, comprising administering to the individual a therapeutically effective amount of an agent that inhibits a tropomyosin receptor kinase (Trk) protein, wherein the NET is associated with a Trk protein that has undergone a genetic translocation or is an NTRK gene fusion protein. In some embodiments, the NTRK gene fusion protein comprises an NTRK1, NTRK2, or NTRK3 tyrosine kinase signaling domain. In some embodiments, the NTRK gene fusion protein is constitutively active. In some embodiments, the NTRK gene fusion protein comprises: (a) an N-terminal polypeptide region comprising a polypeptide sequence other than a TrkA, TrkB, or TrkC polypeptide sequence; and (b) a C-terminal polypeptide region comprising a TrkA, TrkB, or TrkC polypeptide sequence, wherein the C-terminal polypeptide region has TrkA, TrkB, or TrkC kinase activity. In some embodiments, the NTRK gene fusion protein comprises a nucleic acid sequence comprising: (a) a first region corresponding to a sequence from a MPRIP, CD74, RABGAP1L, TPM3, TPR, TFG, PPL, CHTOP, ARHGEF2, NFASC, BCAN, LMNA, TP53, QKI, NACC2, VCL, AGBL4, TRIM24, PAN3, AFAP1, SQSTM1, ETV6, BTBD1, LYN, RBPMS, RFWD2, IRF2BP2, SSBP2, C18ORF8, RNF213, TBC1, DNER, PLEKHA6, PEAR1, MRPL24, MDM4, GRIPAP1, EPS15, DYNC2H1, CEL, EPHB2, EML4, HOMER2, TEL, or FAT1 gene sequence; and (b) a second region corresponding to a NTRK1, NTRK2, or NTRK3 gene sequence.

In the aforementioned methods disclosed herein, in some embodiments, the NTRK gene fusion protein is an ETV6-NTRK gene fusion protein. In some embodiments, the NTRK gene fusion protein comprises: (a) an N-terminal polypeptide region comprising the sequence of a MPRIP, CD74, RABGAP1L, TPM3, TPR, TFG, PPL, CHTOP, ARHGEF2, NFASC, BCAN, LMNA, TP53, QKI, NACC2, VCL, AGBL4, TRIM24, PAN3, AFAP1, SQSTM1, ETV6, BTBD1, LYN, RBPMS, RFWD2, IRF2BP2, SSBP2, C18ORF8, RNF213, TBC1, DNER, PLEKHA6, PEAR1, MRPL24, MDM4, GRIPAP1, EPS15, DYNC2H1, CEL, EPHB2, EML4, HOMER2, TEL, or FAT1 polypeptide sequence; and (b) a C-terminal polypeptide region comprising a TrkA, TrkB, or TrkC polypeptide sequence, wherein the C-terminal polypeptide region has TrkA, TrkB, or TrkC kinase activity. In some embodiments, the N-terminal polypeptide region comprises an ETV6 polypeptide sequence. In some embodiments, the C-terminal polypeptide region comprises a TrkC polypeptide sequence. In some embodiments, the NTRK gene fusion protein comprises: (a) an N-terminal polypeptide region comprising a polypeptide sequence other than a TrkA, TrkB, or TrkC polypeptide sequence; and (b) a C-terminal polypeptide region comprising a TrkA polypeptide sequence, wherein the C-terminal polypeptide comprises TrkA kinase activity; wherein the fusion protein is a TP53-TrkA, LMNA-TrkA, CD74-TrkA, TFG-TrkA, TPM3-TrkA, NFASC-TrkA, BCAN-TrkA, MPRIP-TrkA, TPR-TrkA, RFWD2-TrkA, IRF2BP2-TrkA, SQSTM1-TrkA, SSBP2-TrkA, RABGAP1L-TrkA, C18ORF8-TrkA, RNF213-TrkA, TBC1D22A-TrkA, C20ORF112-TrkA, DNER-TrkA, ARHGEF2-TrkA, CHTOP-TrkA, PPL-TrkA, PLEKHA6-TrkA, PEAR1-TrkA, MRPL24-TrkA, MDM4-TrkA, LRRC71-TrkA, GRIPAP1-TrkA, EPS15-TrkA, DYNC2H1-TrkA, CEL-TrkA, EPHB2-TrkA, or TGF-TrkA fusion protein. In some embodiments, the NTRK gene fusion protein comprises: (a) an N-terminal polypeptide region comprising a polypeptide sequence other than a TrkA, TrkB, or TrkC polypeptide sequence; and (b) a C-terminal polypeptide region comprising a TrkB polypeptide sequence, wherein the C-terminal polypeptide comprises TrkB kinase activity; wherein the fusion protein is a NACC2-TrkB, QKI-TrkB, AFAP1-TrkB, PAN3-TrkB, SQSTM1-TrkB, TRIM24-TrkB, VCL-TrkB, AGBL4-TrkB, or DAB2IP-TrkB fusion protein. In some embodiments, the NTRK gene fusion protein comprises: (a) an N-terminal polypeptide region comprising a polypeptide sequence other than a TrkA, TrkB, or TrkC polypeptide sequence; and (b) a C-terminal polypeptide region comprising a TrkC polypeptide sequence, wherein the C-terminal polypeptide comprises TrkC kinase activity; wherein the fusion protein is a ETV6-TrkC, BTBD1-TrkC, LYN-TrkC, RBPMS-TrkC, EML4-TrkC, HOMER2-TrkC, TFG-TrkC, FAT1-TrkC, or TEL-TrkC fusion protein.

In the aforementioned methods disclosed herein, in some embodiments, the agent that inhibits a Trk protein is a kinase inhibitor. In some embodiments, the agent that inhibits a Trk protein is entrectinib, RXDX-102, altiratinib, larotrectinib, LOXO-195, sitravatinib, cabozantinib, merestinib, dovitinib, crizotinib, TSR-011, DS-6051, PLX7486, lestaurtinib, danusertib, F17752, AZD6918, AZD7451, or AZ-23, or a pharmaceutically acceptable salt thereof. In some embodiments, the agent that inhibits a Trk protein is entrectinib. In some embodiments, the NET is a foregut, midgut, or hindgut NET. In some embodiments, the NET is a gastrointestinal NET. In some embodiments, the NET is a small intestine NET (SI-NET). In some embodiments, the NET is a large intestine NET. In some embodiments, the NET is a rectal intestine NET. In some embodiments, the NET is a gastric intestine NET. In some embodiments, the NET is a pancreatic NET (PNET). In some embodiments, the NET is a bronchial NET. In some embodiments, the NET is an appendix, ovarian, or thyroid NET. In some embodiments, the NET is of unknown primary origin. In some embodiments, the primary NET has metastasized to a secondary tissue. In some embodiments, the secondary tissue is a lymph node, mesentery, liver, bone, lung, or brain. In some embodiments, the agent is utilized as a primary or frontline therapy. In some embodiments, the agent is utilized as a secondary or salvage therapy. In some embodiments, the individual has stable or progressive disease after a previous chemotherapy treatment regimen. In some embodiments, the previous chemotherapy treatment regimen comprises treatment with capecitabine, 5-fluorouracil, doxorubicin, etoposide, dacarbazine, streptozocin, temozolomide, cisplatin, cyclophosphamide, thalidomide, or any combination thereof.

In some embodiments, the aforementioned methods disclosed herein further comprise administering to the individual an additional therapy. In some embodiments, the additional therapy is a second agent that inhibits a Trk protein. In some embodiments, the additional therapy comprises a PI3K/Akt/mTOR pathway inhibitor, a TGF-β pathway inhibitors, a cell cycle inhibitor, a somatostatin analogue, an interferon, or an angiogenesis inhibitor. In some embodiments, the somatostatin analogue is octreotide, octreotate, pasireotide, or lanreotide. In some embodiments, the somatostatin analogue is radiolabeled. In some embodiments, the radiolabeled somatostatin analogue is [DOTA⁰, Tyr³]octreotate (Lutathera). In some embodiments, the interferon is a type I interferon. In some embodiments, the type I interferon is IFN-α. In some embodiments, the additional therapy is everolimus, temsirolimus, bevacizumab, sunitinib, or sorafenib. In some embodiments, the additional therapy comprises surgery, chemotherapy, or radiation therapy. In some embodiments, the individual has a carcinoid syndrome. In some embodiments, the aforementioned methods disclosed herein further comprise administering to the individual a treatment for the carcinoid syndrome. In some embodiments, the treatment for the carcinoid syndrome is an anti-serotonin agent. In some embodiments, the anti-serotonin agent is a somatostatin analogue. In some embodiments, the somatostatin analogue is octreotide, octreotate, pasireotide, or lanreotide.

Disclosed herein, in some embodiments, are methods of treating a neuroendocrine tumor (NET) in an individual in need thereof comprising: (a) obtaining a sample of NET genetic material from the individual; (b) determining whether the NET tumor comprises a NTRK translocation or gene fusion; and (c) administering to the individual an agent that inhibits a tropomyosin receptor kinase (Trk) protein. In some embodiments, the sample of NET genetic material is total nucleic acid obtained from formalin-fixed paraffin-embedded (FFPE) tumor biopsy sample. In some embodiments, the methods disclosed herein further comprise sequencing the NET genetic material to determine whether the tumor sample comprises a NTRK translocation or gene fusion. In some embodiments, the NET genetic material is sequenced by whole genome DNA sequencing, whole exome sequencing, targeted DNA sequencing, targeted RNA sequencing, or whole transcriptome RNA sequencing. In some embodiments, the methods disclosed herein further comprise amplifying the NET genetic material using NTRK1, NTRK2, or NTRK3-specific primers prior to determining whether the NET tumor comprises a NTRK translocation or gene fusion. In some embodiments, the methods disclosed herein further comprise detecting the amount of NTRK expression or Trk protein levels in a NET tumor sample, wherein elevated levels of NTRK expression or Trk protein levels is indicative of a NTRK translocation or gene fusion.

Also disclosed herein, in some embodiments, are methods of treating a gastrointestinal neuroendocrine tumor (NET) in an individual in need thereof, comprising administering to the individual a therapeutically effective amount of an agent that inhibits a tropomyosin receptor kinase (Trk) protein, wherein the NET is associated with a Trk protein that has undergone a genetic translocation or is an NTRK gene fusion protein. In some embodiments, the NTRK gene fusion protein comprises an NTRK1, NTRK2, or NTRK3 tyrosine kinase signaling domain. In some embodiments, the NTRK gene fusion protein is constitutively active. In some embodiments, the NTRK gene fusion protein comprises: (a) an N-terminal polypeptide region comprising a polypeptide sequence other than a TrkA, TrkB, or TrkC polypeptide sequence; and (b) a C-terminal polypeptide region comprising a TrkA, TrkB, or TrkC polypeptide sequence, wherein the C-terminal polypeptide region has TrkA, TrkB, or TrkC kinase activity. In some embodiments, the NTRK gene fusion protein comprises: (a) an N-terminal polypeptide region comprising the sequence of a MPRIP, CD74, RABGAP1L, TPM3, TPR, TFG, PPL, CHTOP, ARHGEF2, NFASC, BCAN, LMNA, TP53, QKI, NACC2, VCL, AGBL4, TRIM24, PAN3, AFAP1, SQSTM1, ETV6, BTBD1, LYN, RBPMS, RFWD2, IRF2BP2, SSBP2, C18ORF8, RNF213, TBC1, DNER, PLEKHA6, PEAR1, MRPL24, MDM4, GRIPAP1, EPS15, DYNC2H1, CEL, EPHB2, EML4, HOMER2, TEL, or FAT1 polypeptide sequence; and (b) a C-terminal polypeptide region comprising a TrkA, TrkB, or TrkC polypeptide sequence, wherein the C-terminal polypeptide region has TrkA, TrkB, or TrkC kinase activity. In some embodiments, the N-terminal polypeptide region comprises an ETV6 polypeptide sequence. In some embodiments, the C-terminal polypeptide region comprises a TrkC polypeptide sequence.

In the aforementioned methods disclosed herein, in some embodiments, the NTRK gene fusion protein comprises: (a) an N-terminal polypeptide region comprising a polypeptide sequence other than a TrkA, TrkB, or TrkC polypeptide sequence; and (b) a C-terminal polypeptide region comprising a TrkA polypeptide sequence, wherein the C-terminal polypeptide comprises TrkA kinase activity; wherein the fusion protein is a TP53-TrkA, LMNA-TrkA, CD74-TrkA, TFG-TrkA, TPM3-TrkA, NFASC-TrkA, BCAN-TrkA, MPRIP-TrkA, TPR-TrkA, RFWD2-TrkA, IRF2BP2-TrkA, SQSTM1-TrkA, SSBP2-TrkA, RABGAP1L-TrkA, C18ORF8-TrkA, RNF213-TrkA, TBC1D22A-TrkA, C20ORF112-TrkA, DNER-TrkA, ARHGEF2-TrkA, CHTOP-TrkA, PPL-TrkA, PLEKHA6-TrkA, PEAR1-TrkA, MRPL24-TrkA, MDM4-TrkA, LRRC71-TrkA, GRIPAP1-TrkA, EPS15-TrkA, DYNC2H1-TrkA, CEL-TrkA, EPHB2-TrkA, or TGF-TrkA fusion protein. In some embodiments, the NTRK gene fusion protein comprises: (a) an N-terminal polypeptide region comprising a polypeptide sequence other than a TrkA, TrkB, or TrkC polypeptide sequence; and (b) a C-terminal polypeptide region comprising a TrkB polypeptide sequence, wherein the C-terminal polypeptide comprises TrkB kinase activity; wherein the fusion protein is a NACC2-TrkB, QKI-TrkB, AFAP1-TrkB, PAN3-TrkB, SQSTM1-TrkB, TRIM24-TrkB, VCL-TrkB, AGBL4-TrkB, or DAB2IP-TrkB fusion protein. In some embodiments, the NTRK gene fusion protein comprises: (a) an N-terminal polypeptide region comprising a polypeptide sequence other than a TrkA, TrkB, or TrkC polypeptide sequence; and (b) a C-terminal polypeptide region comprising a TrkC polypeptide sequence, wherein the C-terminal polypeptide comprises TrkC kinase activity; wherein the fusion protein is a ETV6-TrkC, BTBD1-TrkC, LYN-TrkC, RBPMS-TrkC, EML4-TrkC, HOMER2-TrkC, TFG-TrkC, FAT1-TrkC, or TEL-TrkC fusion protein. In some embodiments, the agent that inhibits a Trk protein is a kinase inhibitor. In some embodiments, the agent that inhibits a Trk protein is entrectinib, RXDX-102, altiratinib, larotrectinib, LOXO-195, sitravatinib, cabozantinib, merestinib, dovitinib, crizotinib, TSR-011, DS-6051, PLX7486, lestaurtinib, danusertib, F17752, AZD6918, AZD7451, or AZ-23, or a pharmaceutically acceptable salt thereof. In some embodiments, the agent is entrectinib, or a pharmaceutically acceptable salt thereof. In some embodiments, the gastrointestinal NET is a small intestine, large intestine, pancreatic, appendix, gastric, rectal, or unknown primary origin NET. In some embodiments, the primary NET has metastasized to a secondary tissue. In some embodiments, the secondary tissue is a lymph node, mesentery, liver, bone, lung, or brain.

Also disclosed herein, in come embodiments, are methods of treating a gastrointestinal neuroendocrine tumor (NET) in an individual in need thereof comprising: (a) obtaining a sample of NET genetic material from the individual; (b) determining whether the NET tumor comprises a NTRK translocation or gene fusion; and (c) administering to the individual a therapeutically effective amount of an agent that inhibits a tropomyosin receptor kinase (Trk) protein. In some embodiments, the sample of NET genetic material is total nucleic acid obtained from formalin-fixed paraffin-embedded (FFPE) tumor biopsy sample. In some embodiments, the methods disclosed herein further comprise sequencing the NET genetic material to determine whether the tumor sample comprises a NTRK translocation or gene fusion. In some embodiments, the NET genetic material is sequenced by whole genome DNA sequencing, whole exome sequencing, targeted DNA sequencing, targeted RNA sequencing, or whole transcriptome RNA sequencing. In some embodiments, the methods disclosed herein further comprise amplifying the NET genetic material using NTRK1, NTRK2, or NTRK3-specific primers prior to determining whether the NET tumor comprises a NTRK translocation or gene fusion. In some embodiments, the methods disclosed herein further comprise detecting the amount of NTRK expression or Trk protein levels in a NET tumor sample, wherein elevated levels of NTRK expression or Trk protein levels is indicative of a NTRK translocation or gene fusion.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A exemplifies FDG-PET imaging of a patient at presentation revealing widespread FDG-uptake in the known areas of disease including a bulky iliac lymphadenopathy with a large left pelvic sidewall confluent mass, multiple hypermetabolic liver lesions, and innumerable lesions throughout the skeleton. FIG. 1B exemplifies FDG-PET imaging of a patient after 2 cycles of entrectinib treatment showing improvement in the previously confluent bony disease (compare right proximal femur) and decreased bulk and intensity in the pelvic lymphadenopathy. The most intense activity observed in the pelvis after entrectinib treatment is the elongated bladder, deviated to the right.

FIG. 2A exemplifies anterior and posterior octreoscan imaging of a patient at presentation (anterior and posterior, planar) revealing widespread distribution of disease including extensive skeletal metastases and a bulky pelvic lymphadenopathy. FIG. 2B exemplifies anterior and posterior octreoscan imaging of a patient after 6 cycles of entrectinib treatment. Although the patient still exhibited signs of disease in the liver, bones, and pelvis, there was significant overall reduction in tumor burden compared with the presentation octreoscan. The largest and most active foci correspond with the bulky left pelvic sidewall and pre-sacral masses.

FIGS. 3A-B exemplify an enhanced axial abdominal CT of a patient. FIG. 3A exemplifies an enhanced axial abdominal CT obtained after an initial trial of temozolomide and capecitabine chemotherapy demonstrating bulky enhancing left pelvic sidewall and pre-sacral nodal masses. FIG. 3B exemplifies an enhanced axial abdominal CT obtained after 1 cycle of entrectinib treatment demonstrating a dramatic change in appearance of the left pelvic sidewall masses, which appear swollen and measure larger, but are lower in density.

DETAILED DESCRIPTION OF THE INVENTION

Figure 1A:
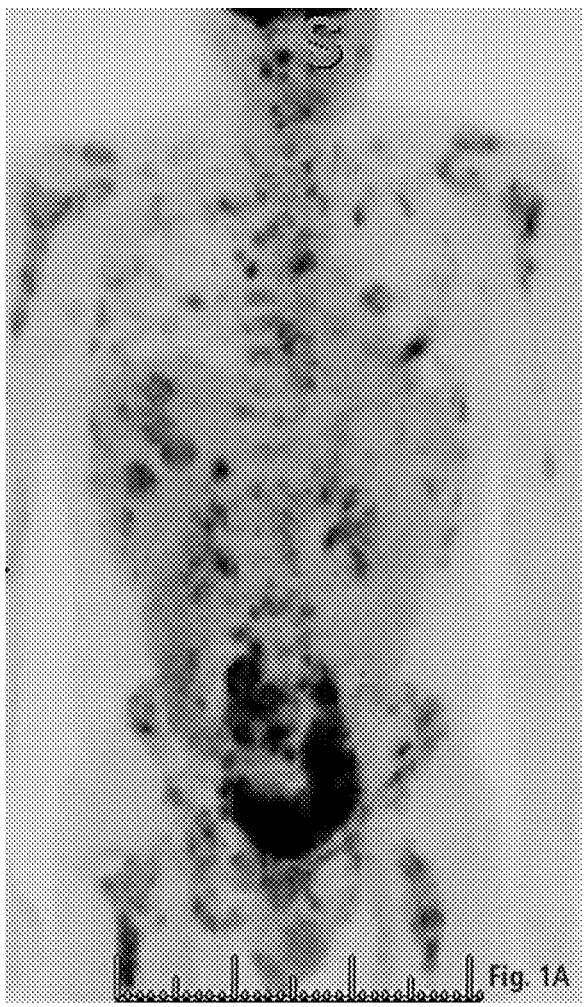
FIGS. 1A-B exemplify FDG-PET imaging of a patient.

The overexpression, activation, mutation, or translocation of tropomyosin receptor kinase (Trk) family members TrkA, TrkB, and TrkC have been reported in many different cancer types, including ovarian cancer, colorectal cancer, melanoma, and lung cancer. In preclinical models of cancer, Trk inhibitors are efficacious at inhibiting both tumor growth and tumor metastasis. Neuroendocrine tumors (NETs) are a rare, slow growing form of cancer that arises from neuroendocrine cells distributed throughout the body. NETs as a whole are a heterogeneous group of neoplasms whose characteristics can vary dependent upon the tissue of origin. To date, no definitive oncogenic drivers or indications of molecular parthenogenesis have been identified for the vast majority of NETs.

Disclosed herein, in some embodiments, are methods of treating a neuroendocrine tumor (NET) in an individual in need thereof, comprising administering to the individual a therapeutically effective amount of an agent that inhibits a tropomyosin receptor kinase (Trk) protein, wherein the NET is associated with a Trk protein that has undergone a genetic translocation or is an NTRK gene fusion protein. Also disclosed herein, in some embodiments, are methods of treating a neuroendocrine tumor (NET) in an individual in need thereof comprising: (a) obtaining a sample of NET genetic material from the individual; (b) determining whether the NET tumor comprises a NTRK translocation or gene fusion; and (c) administering to the individual a therapeutically effective amount of an agent that inhibits a tropomyosin receptor kinase (Trk) protein.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an," and "the" include plural referents unless the context clearly dictates otherwise. Furthermore, the use of "or" means "and/or" unless stated otherwise. Use of the term "including" as well as other forms, such as "include," "includes," and "included," is not intended to be limited solely to the recited items. The section headings used herein are for organizational purposes only and are not to be construed as limiting the subject matter described.

The terms "effective amount" or "therapeutically effective amount," as used herein, refer to a sufficient amount of an agent or a compound (e.g., the NTRK inhibitors described herein) being administered which will relieve, to some extent, one or more of the symptoms of the disease or condition being treated. The result can be reduction and/or alleviation of the signs, symptoms, or causes of a disease, or any other desired alteration of a biological system. The terms "effective amount" or "therapeutically effective amount" include, for example, a prophylactically effective amount.

The terms "about" or "approximately," as used herein, mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, and more preferably within 2-fold of a value.

The terms "subject," "individual," and "patient" are used interchangeably herein to refer to a vertebrate, preferably a mammal, more preferably a human. In some embodiments, mammals include, but are not limited to, murines, simians, humans, farm animals, sport animals, and pets. In some embodiments, tissues, cells, and their progeny of a biological entity obtained in vivo or cultured in vitro are encompassed. None of these terms, as used herein, entail supervision of a medical professional.

Neuroendocrine Tumors (NETs)

Neuroendocrine cells are highly specialized nerve-like cells that release hormones in response to a neurological or chemical signal. The neuroendocrine system is made up of a network of neuroendocrine cells organized both in single organs and as diffuse elements widely distributed throughout the body. For example, neuroendocrine cells are scattered throughout the gastrointestinal tract and secrete hormones (e.g., serotonin) that regulate intestinal movements. On the other hand, the pituitary is a neuroendocrine gland that secretes hormones (e.g., growth hormone) that regulate several physiological processes, including growth, blood pressure, and metabolism.

Neuroendocrine tumors (NETs) are rare, typically slow-growing neoplasms composed of neuroendocrine cells. NETs originate from a wide variety of organs and are among the most frequent types of small bowel neoplasm. In some instances, NETs are referred to as "carcinoid tumors," which generally refer to NETs originating from the diffuse neuroendocrine system, primarily the gastrointestinal and respiratory tracts. The most common location of gastrointestinal NETs are in the small intestine, most often in the ileum, but NETs also frequently originate in the rectum, colon, appendix, and stomach.

Contemporary understanding of NETs is clouded by the lack of a standardized nomenclature, staging, and grading systems. Furthermore, because NETs are a rare form of cancer and often exhibit nonspecific clinical manifestations, NETs are frequently overlooked in the differential diagnosis. Moreover, even small NETs (<2 cm) can be aggressive and readily metastasize presenting considerable challenges to the diagnosing clinician. Most studies on NETs are focused upon the most frequent locations, such as the pancreas and small intestinal, limiting extensive knowledge of other less common forms of the disease.

While some features are shared in common by all NETs, others are attributable to their organ of origin (e.g., gastrointestinal NETs tend to be genomically stable while pancreatic NETs exhibit frequent chromosomal instability). With this degree of clinical heterogeneity, the molecular pathogenesis of NETs remains elusive and definitive oncogenic drivers of disease have yet to be identified. While most pancreatic or gastrointestinal NETs arise sporadically, a number of hereditary conditions are risk factors for development the disease. For example, multiple endocrine neoplasia type 1 (inherited MEN1 mutations), neurofibromatosis type 1 (inherited NF1 mutations), von Hippel-Lindau disease (inherited VHL mutations), and tuberous sclerosis (inherited TSC1 or TSC2 mutations) are all conditions that increase the likelihood of NETs.

Disclosed herein, in some embodiments, are methods of treating a neuroendocrine tumor (NET) in an individual in need thereof, comprising administering to the individual a therapeutically effective amount of an agent that inhibits a tropomyosin receptor kinase (Trk) protein, wherein the NET is associated with a Trk protein that has undergone a genetic translocation or is an NTRK gene fusion protein. Also disclosed herein, in some embodiments, are methods of treating a neuroendocrine tumor (NET) in an individual in need thereof comprising: (a) obtaining a sample of NET genetic material from the individual; (b) determining whether the NET tumor comprises a NTRK translocation or gene fusion; and (c) administering to the individual a therapeutically effective amount of an agent that inhibits a tropomyosin receptor kinase (Trk) protein.

In some embodiments, the NET is a foregut, midgut, or hindgut NET. In some embodiments, the NET is a gastrointestinal tract NET. In some embodiments, the NET is a small intestine NET (SI-NET). In some embodiments, the NET is a large intestine NET. In some embodiments, the NET is a pancreatic NET (PNET). In some embodiments, the NET is a NET of the appendix. In some embodiments, the NET is a gastric NET. In some embodiments, the NET is a rectal NET. In some embodiments, the NET is a bronchial NET. In some embodiments, the NET is an ovarian NET. In some embodiments, the NET is a NET of the thyroid. In some embodiments, the NET is an unknown primary NET, wherein the organ of origin cannot be identified. In some embodiments, the primary NET has metastasized to a secondary tissue. In some embodiments, the secondary tissue is lymph node, mesentery, liver, bone, lung, or brain.

Carcinoid Syndrome

Carcinoid syndrome can develop in some individuals harboring a NET, typically in those with advanced or metastasized NETs. Carcinoid syndrome is caused by the unregulated secretion of hormones into the bloodstream from NET cells that cause a variety of signs and symptoms depending upon the type of NET. The most common signs and symptoms of carcinoid syndrome include skin flushing, facial skin lesions, diarrhea, difficulty breathing, and rapid heartbeat. Delayed diagnosis, or misdiagnosis, occurs frequently in patients with carcinoid syndrome, as symptoms may be mistaken for other diseases, such as irritable bowel syndrome (IBS) or menopause.

In some embodiments, the individual has a carcinoid syndrome. In some embodiments, the methods described herein further comprise administered a treatment for the carcinoid syndrome. In some embodiments, the treatment for the carcinoid syndrome is an anti-serotonin agent. In some embodiments, the anti-serotonin agent is a somatostatin analogue. In some embodiments, the somatostatin analogue is octreotide, octreotate, pasireotide, or lanreotide.

NTRK Translocations and Gene Fusions

The tropomyosin receptor kinase (Trk or TRK) family of tyrosine kinase receptors are multi-domain transmembrane proteins that play an important role in a wide spectrum of neuronal responses including survival, differentiation, growth, and regeneration. The Trk receptors are expressed abundantly in the nervous system, as well as in many other non-neuronal cell types and tissues, including monocytes, the lung, bone, and pancreatic beta cells. There are three members of the Trk family: TrkA, TrkB, and TrkC, encoded by the NTRK1, NTRK2, and NTRK3 genes respectively. TrkA, TrkB, and TrkC are characterized as high affinity receptors for naturally occurring neurotrophins, a family of protein growth factors which includes nerve growth factor (NGF), brain derived neurotrophic factor (BDNF), neurotrophin-3 (NT-3), and neurotrophins-4/5 (NT-4/5). Mature neurotrophins bind a selective Trk receptor with relatively high affinity (e.g., TrkB-BDNF, TrkA-NGF, and TrkC-NT-3), resulting in the activation of intracellular tyrosine kinase signaling cascades (e.g., SHC-RAS-MAPK, PI3K-AKT, or PLCγ-PKC) that mediate neurotrophin function (e.g., neuronal growth and survival).

NTRK Translocations and Gene Fusion Proteins

Gene fusion, the process by which complete or partial sequences of two or more distinct genes are fused into a single chimeric gene or transcript, can be the result of a translocation, deletion, or inversion. While some gene fusion products are passive, resulting in no noticeable phenotypic changes, others have been shown to have oncogenic activity. The prevalence of gene fusions in cancer varies widely between different cancer types. For example, the TMPRSS2-ERG fusion is found in over 50% of all prostate cancer patients. Alternatively, some gene fusions, such as the KIF5B-RET fusion, are found in only 1-2% of lung adenocarcinomas.

Oncogenic activity arising from translations or gene fusion events are typically due to the deregulation of one of the involved genes (e.g., fusing a strong promoter to a proto-oncogene), inducing a loss of function (e.g., by truncation of a tumor suppressor gene), or forming a fusion protein with oncogenic functionality (e.g., causing constitutive activation of a tyrosine kinase, such as the NTRK genes described herein). The typical gene structure for an oncogenic tyrosine kinase gene fusion is where the catalytic kinase domain (C-terminal intracellular region of a receptor tyrosine kinase) is fused with an N-terminal region derived from another gene. The resultant novel oncogene is aberrantly expressed by the foreign promoter and can result in the constitutive activation of the kinase domain (e.g., through fusion protein dimerization mediated by the N-terminal domain).

The NTRK family of genes are promiscuous gene fusion partners and are known to generate a variety of oncogenic translocations and fusion proteins. Disclosed herein, in some embodiments, are methods of treating a neuroendocrine tumor (NET) in an individual in need thereof, comprising administering to the individual a therapeutically effective amount of an agent that inhibits a tropomyosin receptor kinase (Trk) protein, wherein the NET is associated with a Trk protein that has undergone a genetic translocation or is an NTRK gene fusion protein. Also disclosed herein, in some embodiments, are methods of treating a neuroendocrine tumor (NET) in an individual in need thereof comprising: (a) obtaining a sample of NET genetic material from the individual; (b) determining whether the NET tumor comprises a NTRK translocation or gene fusion; and (c) administering to the individual a therapeutically effective amount of an agent that inhibits a tropomyosin receptor kinase (Trk) protein.

In some embodiments, the NTRK translocation is a translocation of at least a portion of an NTRK1, NTRK2, or NTRK3 gene to another location within the same chromosome (including inversions). In some embodiments, the NTRK translocation is a translocation of at least a portion of an NTRK1, NTRK2, or NTRK3 gene to a different chromosome. In some embodiments, the NTRK translocation is a translocation of at least a portion of an NTRK1, NTRK2, or NTRK3 gene that results in an NTRK1, NTRK2, or NTRK3 gene under the transcriptional control of a foreign promoter, resulting in aberrant NTRK expression. In some embodiments, the NTRK translocation results in a constitutively active NTRK1, NTRK2, or NTRK3 gene.

In some embodiments, an NTRK fusion protein (also referred to as a Trk fusion protein) is generated by the genetic translocation of at least a portion of an NTRK1, NTRK2, or NTRK3 gene with at least a portion of another gene. In some embodiments, the NTRK fusion protein comprises an NTRK1, NTRK2, or NTRK3 tyrosine kinase signaling domain. In some embodiments, the NTRK fusion protein is under the transcriptional control of a foreign promoter, resulting in aberrant NTRK expression. In some embodiments, the NTRK fusion protein results in a constitutively active NTRK gene. In some embodiments, the NTRK fusion protein comprises an N-terminal region that corresponds to a protein other than a TrkA, TrkB, or TrkC protein and a C-terminal region that corresponds to a TrkA, TrkB, or TrkC protein. In some embodiments, the C-terminal region corresponding to a TrkA, TrkB, or TrkC protein has TrkA, TrkB, or TrkC kinase activity. The phrase "kinase activity," as used herein, means having the activity of a kinase enzyme as understood by those having skill in the art, and includes, e.g., the phosphorylation of amino acid side chains, such as serine, threonine, or tyrosine. In some embodiments, the NTRK fusion protein results in a constitutively active TrkA, TrkB, or TrkC fusion protein. In some embodiments, the constitutively active TrkA, TrkB, or TrkC fusion protein comprises an N-terminal region from a protein other than TrkA, TrkB, or TrkC, that causes dimerization of the Trk fusion protein.

In some embodiments, the NTRK fusion protein comprises a nucleic acid sequence comprising: (a) a first region corresponding to a sequence from a MPRIP, CD74, RABGAP1L, TPM3, TPR, TFG, PPL, CHTOP, ARHGEF2, NFASC, BCAN, LMNA, TP53, QKI, NACC2, VCL, AGBL4, TRIM24, PAN3, AFAP1, SQSTM1, ETV6, BTBD1, LYN, RBPMS, RFWD2, IRF2BP2, SSBP2, C18ORF8, RNF213, TBC1, DNER, PLEKHA6, PEAR1, MRPL24, MDM4, GRIPAP1, EPS15, DYNC2H1, CEL, EPHB2, EML4, HOMER2, TEL, or FAT1 gene sequence; and (b) a second region corresponding to a NTRK1, NTRK2, or NTRK3 gene sequence.

In some embodiments, the NTRK fusion protein comprises a nucleic acid sequence comprising: (a) a first region corresponding to a portion of the sequence from a MPRIP, CD74, RABGAP1L, TPM3, TPR, TFG, PPL, CHTOP, ARHGEF2, NFASC, BCAN, LMNA, TP53, QKI, NACC2, VCL, AGBL4, TRIM24, PAN3, AFAP1, SQSTM1, ETV6, BTBD1, LYN, RBPMS, RFWD2, IRF2BP2, SSBP2, C18ORF8, RNF213, TBC1, DNER, PLEKHA6, PEAR1, MRPL24, MDM4, GRIPAP1, EPS15, DYNC2H1, CEL, EPHB2, EML4, HOMER2, TEL, or FAT1 gene sequence;

and (b) a second region corresponding to a portion of a NTRK1, NTRK2, or NTRK3 gene sequence.

In some embodiments, the NTRK fusion protein comprises: (a) an N-terminal polypeptide region comprising a polypeptide sequence other than a TrkA, TrkB, or TrkC polypeptide sequence; and (b) a C-terminal polypeptide region comprising a TrkA, TrkB, or TrkC polypeptide sequence, wherein the C-terminal polypeptide region has TrkA, TrkB, or TrkC kinase activity. In some embodiments, the NTRK fusion protein comprises: (a) an N-terminal polypeptide region comprising the sequence of a MPRIP, CD74, RABGAP1L, TPM3, TPR, TFG, PPL, CHTOP, ARHGEF2, NFASC, BCAN, LMNA, TP53, QKI, NACC2, VCL, AGBL4, TRIM24, PAN3, AFAP1, SQSTM1, ETV6, BTBD1, LYN, RBPMS, RFWD2, IRF2BP2, SSBP2, C18ORF8, RNF213, TBC1, DNER, PLEKHA6, PEAR1, MRPL24, MDM4, GRIPAP1, EPS15, DYNC2H1, CEL, EPHB2, EML4, HOMER2, TEL, or FAT1 polypeptide sequence; and (b) a C-terminal polypeptide region comprising a TrkA, TrkB, or TrkC polypeptide sequence, wherein the C-terminal polypeptide region has TrkA, TrkB, or TrkC kinase activity. In some embodiments, the NTRK fusion protein is an ETV6:NTRK fusion protein and comprises an N-terminal polypeptide region comprising an ETV6 polypeptide sequence and a C-terminal polypeptide region comprising a TrkA, TrkB, or TrkC polypeptide sequence, wherein the C-terminal polypeptide region has TrkA, TrkB, or TrkC kinase activity.

In some embodiments, the Trk fusion protein comprises (a) an N-terminal polypeptide region comprising a polypeptide sequence other than a TrkA, TrkB, or TrkC polypeptide sequence; and (b) a C-terminal polypeptide region comprising a TrkA polypeptide sequence, wherein the C-terminal polypeptide comprises TrkA kinase activity; and wherein the fusion protein is a TP53-TrkA, LMNA-TrkA, CD74-TrkA, TFG-TrkA, TPM3-TrkA, NFASC-TrkA, BCAN-TrkA, MPRIP-TrkA, TPR-TrkA, RFWD2-TrkA, IRF2BP2-TrkA, SQSTM1-TrkA, SSBP2-TrkA, RABGAP1L-TrkA, C18ORF8-TrkA, RNF213-TrkA, TBC1D22A-TrkA, C20ORF112-TrkA, DNER-TrkA, ARHGEF2-TrkA, CHTOP-TrkA, PPL-TrkA, PLEKHA6-TrkA, PEAR1-TrkA, MRPL24-TrkA, MDM4-TrkA, LRRC71-TrkA, GRIPAP1-TrkA, EPS15-TrkA, DYNC2H1-TrkA, CEL-TrkA, EPHB2-TrkA, or TGF-TrkA fusion protein.

In some embodiments, the Trk fusion protein comprises (a) an N-terminal polypeptide region comprising a polypeptide sequence other than a TrkA, TrkB, or TrkC polypeptide sequence; and (b) a C-terminal polypeptide region comprising a TrkB polypeptide sequence, wherein the C-terminal polypeptide comprises TrkB kinase activity; and wherein the fusion protein is a NACC2-TrkB, QKI-TrkB, AFAP1-TrkB, PAN3-TrkB, SQSTM1-TrkB, TRIM24-TrkB, VCL-TrkB, AGBL4-TrkB, or DAB2IP-TrkB fusion protein.

In some embodiments, the Trk fusion protein comprises (a) an N-terminal polypeptide region comprising a polypeptide sequence other than a TrkA, TrkB, or TrkC polypeptide sequence; and (b) a C-terminal polypeptide region comprising a TrkC polypeptide sequence, wherein the C-terminal polypeptide comprises TrkC kinase activity; and wherein the fusion protein is a ETV6-TrkC, BTBD1-TrkC, LYN-TrkC, RBPMS-TrkC, EML4-TrkC, HOMER2-TrkC, TFG-TrkC, FAT1-TrkC, or TEL-TrkC fusion protein. In some embodiments, the Trk fusion protein is an ETV6-NTRK3 (ETV6-TrkC) fusion protein.

Methods of Treatment

Disclosed herein, in some embodiments, are methods of treating a neuroendocrine tumor (NET) in an individual in need thereof, comprising administering to the individual a therapeutically effective amount of an agent that inhibits a tropomyosin receptor kinase (Trk) protein, wherein the NET is associated with a Trk protein that has undergone a genetic translocation or is an NTRK gene fusion protein. Also disclosed herein, in some embodiments, are methods of treating a neuroendocrine tumor (NET) in an individual in need thereof comprising: (a) obtaining a sample of NET genetic material from the individual; (b) determining whether the NET tumor comprises a NTRK translocation or gene fusion; and (c) administering to the individual a therapeutically effective amount of an agent that inhibits a tropomyosin receptor kinase (Trk) protein.

In some embodiments, the agent that inhibits a tropomyosin receptor kinase (Trk) protein is entrectinib. Entrectinib (RXDX-101/NMS-E628) is a selective inhibitor of the TrkA, TrkB, and TrkC receptor tyrosine kinases encoded by the NTRK1-3 genes respectively. In addition to its activity against native Trk proteins, entrectinib is also an effective inhibitor of Trk fusion proteins generated by, e.g., genetic translocations or rearrangements of the NTRK genes. Entrectinib also inhibits the ROS1 and ALK proteins and ROS1 and ALK gene fusion products. Entrectinib is a substituted indazole derivative with a chemical name of N-[5-(3,5-difluoro-benzyl)-1h-indazol-3-yl]-4-(4-methyl-piperazin-1-yl)-2-(tetrahydro-pyran-4-ylamino)-benzamide. See U.S. Pat. No. 8,299,057 incorporated by reference herein, for a description of entrectinib and other substituted indazole derivative kinase inhibitors useful as agents in accordance with the present disclosure.

In some embodiments, the agent that inhibits a Trk protein is RXDX-102 (NMS-P360). RXDX-102 is an orally available, selective tyrosine kinase inhibitor designed as an oncogene-targeted therapeutic candidate to treat patients with cancers harboring activating alterations to the TrkA, TrkB or TrkC proteins.

In some embodiments, the agent that inhibits a Trk protein is altiratinib (DCC-2701). Altiratinib is a kinase inhibitor designed to simultaneously block multiple cancer signaling mechanisms in the tumor cell and tumor microenvironment to prevent growth and spread of cancer. Altiratinib is a MET, TIE2, VEGFR2 and TrkA/B/C kinase inhibitor with a chemical name of N-[4-[2-(cyclopropanecarboxamido)pyridin-4-yl]oxy-2,5-difluorophenyl]-N-(4-fluorophenyl)cyclopropane-1,1-dicarboxamide. See U.S. Pat. No. 8,637,672 incorporated by reference herein, for a description of altiranib and other cyclopropyl dicarboxamide compounds and analogs useful as agents in accordance with the present disclosure.

In some embodiments, the agent that inhibits a Trk protein is larotrectinib (LOXO-101/ARRY-470). Larotrectinib is a selective Trk kinase inhibitor currently being tested in advanced solid tumors harboring NTRK fusions and has a chemical name of (S)—N-[5-[(R)-2-(2,5-difluorophenyl) pyrrolidin-1-yl]pyrazolo[1,5-a]pyrimidin-3-yl]-3-hydroxy-pyrrolidine-1-carboxamide. See U.S. Pat. No. 8,513,263 incorporated by reference herein, for a description of larotrectinib and other substituted pyrazolo[1,5-a]pyrimidine compounds useful as agents in accordance with the present disclosure.

In some embodiments, the agent that inhibits a Trk protein is LOXO-195. LOXO-195 is a next-generation, selective TRK inhibitor that demonstrates potent inhibition of TRK fusion proteins and is unaffected by certain acquired resistance mutations (e.g., TrkA G595R, TrkA G667C, or TrkC G623R) that may emerge in patients receiving larotrectinib (LOXO-101) or multikinase inhibitors with anti-TRK activity.

In some embodiments, the agent that inhibits a Trk protein is sitravatinib (MGCD516). Sitravatinib is a clinical stage, orally available, potent small molecule kinase inhibitor targeting a closely related spectrum of tyrosine kinases, including RET, CBL, CHR4q12, DDR, and TRK. Sitravatinib effectively inhibits TRK fusion proteins and has a chemical name of N-[3-fluoro-4-[2-[5-[(2-methoxyethyl-amino)methyl]pyridin-2-yl]thieno[3,2-b]pyridin-7-yloxy]phenyl]-N-(4-fluorophenyl)cyclopropane-1,1-dicarboxamide. See U.S. Pat. No. 8,404,846 incorporated by reference herein, for a description of sitravatinib and other compounds useful as agents in accordance with the present disclosure.

In some embodiments, the agent that inhibits a Trk protein is cabozantinib (XL184). Cabozantinib is an orally available, small molecule kinase inhibitor of RET, MET, VEGFR-1/2/3, KIT, TRKB, FLT-3, AXL, and TIE-2. Cabozantinib is clinically approved for the treatment of patients with advanced renal cell carcinoma (RCC) or progressive, metastatic medullary thyroid cancer and has a chemical name of N-(4-(6,7-dimethoxyquinolin-4-yloxy)phenyl)-N'-(4-fluorophenyl)cyclopropane-1,1-dicarboxamide. See U.S. Pat. No. 7,579,473 incorporated by reference herein, for a description of cabozantinib and other compounds useful as agents in accordance with the present disclosure.

In some embodiments, the agent that inhibits a Trk protein is merestinib (LY2801653). Merestinib is an orally available, small molecule kinase inhibitor that disrupts signal transduction of MET, MST1R, FLT3, AXL, MERTK, TEK, ROS1, TRKA/B/C, DDR1/2 and MKNK1/2. Merestinib is currently being tested as treatment for advanced solid tumor in patients with NTRK rearrangements and has a chemical name of N-(3-fluoro-4-(1-methyl-6-(1H-pyrazol-4-yl)-1H-indazol-5-yloxy)phenyl)-1-(4-fluorophenyl)-6-methyl-2-oxo-1,2-dihydropyridine-3-carboxamide. See U.S. Pat. No. 8,030,302 incorporated by reference herein, for a description of merestinib and other amidophenoxyindazole compounds useful as agents in accordance with the present disclosure.

In some embodiments, the agent that inhibits a Trk protein is dovitinib (TKI258). Dovitinib is a benzimidazole-quinolinone small molecule kinase inhibitor inhibitor with potential antineoplastic activity. Dovitinib binds to and inhibits the phosphorylation of FGFR, PDGFR, VEGF, cKIT, FLT3, CSFR1, Trk, and RET and is being tested in the clinic for treatment of solid tumors and/or hematologic malignancies having NTRK1 translocations.

In some embodiments, the agent that inhibits a Trk protein is crizotinib. Crizotinib is an orally available, small molecule kinase inhibitor approved for the treatment of patients with locally advanced or metastatic ALK-positive non-small cell lung cancer (NSCLC). Crizotinib is an inhibitor of TRKA in addition to ALK, MET and ROS1 and has been utilized in the treatment of a NSCLC with a MPRIP-NTRK1 fusion. Crizotinib has a chemical name of (R)-3-[1-(2,6-dichloro-3-fluorophenyl)ethoxy]-5-[1-(piperidin-4-yl)-1H-pyrazol-4-yl]pyridin-2-amine. See U.S. Pat. No. 8,785,632 incorporated by reference herein, for a description of crizotinib and other enantiomerically pure aminoheteroaryl compounds useful as agents in accordance with the present disclosure.

In some embodiments, the agent that inhibits a Trk protein is TSR-011. TSR-011 (Tesoro, Inc.) is an orally available, small molecule kinase inhibitor of ALK and TRK-A/B/C. TSR-011 is presently undergoing a phase I/IIa trial for patients with advanced solid tumors or lymphomas with NTRK alterations.

In some embodiments, the agent that inhibits a Trk protein is DS-6051. DS-6051 (Daiichi Sankyo, Inc.) is an orally available kinase inhibitor of ROS1 and TRKs. DS-6051 is in early clinical testing for the treatment of advanced solid malignant tumors harboring either a ROS1 or NTRK gene fusion.

In some embodiments, the agent that inhibits a Trk protein is PLX7486. PLX7486 (Plexxikon) is an orally available kinase inhibitor in early clinical testing for the treatment of advanced solid malignant tumors with activating Trk (NTRK) mutations or NTRK gene fusions.

In some embodiments, the agent that inhibits a Trk protein is lestaurtinib (CEP-701). Lestaurtinib is an orally available indolocarbazole derivative kinase inhibitor of FLT3, JAK2, and TrkA/B/C.

In some embodiments, the agent that inhibits a Trk protein is danusertib (PHA-739358), F17752 (Pierre Fabre), AZD6918 (Astra Zeneca), AZD7451 (Astra Zeneca), or AZ-23 (CAS#: 915720-21-7).

A variety of pharmaceutically acceptable salts, carriers, or excipients of the aforementioned Trk inhibitors are available and any suitable pharmaceutically acceptable salt, carrier, or excipient is contemplated for use with the Trk inhibitors disclosed herein.

In some embodiments, the agent that inhibits a tropomyosin receptor kinase (Trk) protein is utilized as a primary or frontline therapy. In some embodiments, the agent that inhibits a Trk protein is utilized as a secondary or salvage therapy. In some embodiments, the agent that inhibits a Trk protein is utilized as a secondary or salvage therapy, wherein the individual has stable or progressive disease after a previous chemotherapy treatment regimen. A variety of chemotherapeutic agents are available and known in the art and any suitable chemotherapy is contemplated for use with the methods disclosed herein. Exemplary chemotherapy treatment regimens include, but are not limited to, capecitabine, 5-fluorouracil, doxorubicin, etoposide, dacarbazine, streptozocin, temozolomide, cisplatin, cyclophosphamide, thalidomide, or any combination thereof.

Disclosed herein, in some embodiments, are methods of treating a neuroendocrine tumor (NET) in an individual in need thereof, comprising administering to the individual a therapeutically effective amount of an agent that inhibits a tropomyosin receptor kinase (Trk) protein, wherein the NET is associated with a Trk protein that has undergone a genetic translocation or is an NTRK gene fusion protein. Also disclosed herein, in some embodiments, are methods of treating a neuroendocrine tumor (NET) in an individual in need thereof comprising: (a) obtaining a sample of NET genetic material from the individual; (b) determining whether the NET tumor comprises a NTRK translocation or gene fusion; and (c) administering to the individual a therapeutically effective amount of an agent that inhibits a tropomyosin receptor kinase (Trk) protein.

In some embodiments, the methods identifying a NTRK translocation or gene fusion comprises the use of a microarray, expressed sequence tag (EST) mapping, karyotyping, cytogenetic analysis, phosphotyrosine signaling screening, phosphoproteome analysis, chromatin interaction analysis, mass spectrophotometry, tandem mass spectrophotometry analysis, quantitative PCR (qPCR), digital PCR, droplet digital PCR (e.g., Raindance RainDrop Plus™ or Bio-Rad QX200™ Droplet Digital™ PCR), fluorescence in situ hybridization assay (FISH), or any combinations thereof. In some embodiments, a method to identify a NTRK translocation or gene fusion comprises sequencing tumor genetic material. In some embodiments, the tumor sample is subjected to DNA sequencing, whole genome sequencing, exome sequencing, or RNA sequencing to determine whether the tumor sample comprises a NTRK translocation or gene fusion.

A variety of sequencing technologies and techniques are available and any suitable sequencing technology is contemplated for use with the methods disclosed herein. In some embodiments, the sequencing technology is a dye terminator based sequencing methodology (e.g., Sanger sequencing). In some embodiments, the sequencing technology is a next generation sequencing (NGS) method. In some embodiments, the next generation sequencing method is pyrosequencing (e.g., Roche's 454 systems), sequencing by synthesis (e.g., Illumina's GA/HiSeq/MiSeq/NextSeq systems), sequencing by ligation (e.g., Applied Biosystem's SOLiD systems), sequencing by detection of hydrogen ions released during polymerization of DNA (e.g., Ion Torrent sequencing systems), single molecule sequencing (e.g., Pacific Biosciences sequencing systems), or any combinations thereof. In some embodiments, the genetic material is DNA or complementary DNA (cDNA). In some embodiments, the cDNA is reverse transcribed from RNA. In some embodiments, sequencing comprises whole genome sequencing (WGS), whole exome sequencing (WES), whole genome transcriptome sequencing (RNAseq), a targeted sequencing approach, or any combinations thereof. In some embodiments, a particular target is enriched from the isolated tumor genetic material (e.g., the exome, or more preferably, NTRK containing exons). In some embodiments, the genetic material is amplified prior to NTRK fusion detection by, e.g., DNA or RNA sequencing.

In some embodiments, the genetic material is broken into a plurality of nucleic acid fragments prior to sequencing (e.g., by NGS) to create a sequencing library. A variety of library preparation techniques are available, and any suitable method to create the sequencing library is contemplated for use with the methods disclosed herein. In some embodiments, the plurality of nucleic acid fragments are size selected prior to sequencing. In some embodiments, the plurality of nucleic acid fragments comprise barcodes used to identify the plurality of fragments, e.g., in a multiplexed reaction containing differing samples. In some embodiments, the barcodes are molecule-level barcodes. In some embodiments, the barcodes are sample-level barcodes. In some embodiments, sequencing the genetic material comprises sequencing one end of the plurality of nucleic acid fragments (single-end). In some embodiments, sequencing the genetic material comprises sequencing both ends of the plurality of nucleic acid fragments (paired-end or mate-pair). In some embodiments, the method identifying a NTRK translocation or gene fusion comprises paired-end RNA sequencing (PE RNAseq).

In some embodiments, high-throughput sequencing methods are paired with computational tools for identifying NTRK translocations or gene fusions. A variety of computational tools are available and any suitable computation tool is contemplated for use with the methods disclosed herein. Exemplary computational tools include, but are not limited to, FusionMetaCaller, INTEGRATE, IDP-fusion, JAFFA, TRUP, ChildDecode, FusionCatcher, PRADA, EBARDenovo, FusionQ, iFUSE, SOAPFuse, SOAPfusion, Bellerophontes, BreakFusion, elDorado, EricScript, FusionAnalyser, FusionFinder, LifeScope, nFuse, ChimeraScan, Comrad, deFuse, FusionHunter, FusionMap, ShortFuse, SnowShoes-FTD, TopHat-Fusion, FusionSeq, or any combinations thereof. In some embodiments, the gene fusion is verified using polymerase chain reaction (PCR), e.g., by PCR, RT-PCR, qPCR, or any combinations thereof.

Combination Therapies

Disclosed herein, in some embodiments, are methods of treating a neuroendocrine tumor (NET) in an individual in need thereof, comprising administering to the individual a therapeutically effective amount of an agent that inhibits a tropomyosin receptor kinase (Trk) protein, wherein the NET is associated with a Trk protein that has undergone a genetic translocation or is an NTRK gene fusion protein. Also disclosed herein, in some embodiments, are methods of treating a neuroendocrine tumor (NET) in an individual in need thereof comprising: (a) obtaining a sample of NET genetic material from the individual; (b) determining whether the NET tumor comprises a NTRK translocation or gene fusion; and (c) administering to the individual a therapeutically effective amount of an agent that inhibits a tropomyosin receptor kinase (Trk) protein.

In some embodiments, the method further comprises administering an additional therapy to the individual. In some embodiments, the additional therapy is a second agent that inhibits a Trk protein (e.g., the Trk inhibitors disclosed herein). In some embodiments, the NET has primary resistance to an agent that inhibits a Trk protein. In some embodiments, the NET develops acquired (secondary) resistance to an agent that inhibits a Trk protein. In some embodiments, the NET with acquired resistance to an agent that inhibits a Trk protein comprises a mutation in the kinase domain of a Trk protein. In some embodiments, the mutation in the kinase domain is a TrkA G595R or G667C mutation. In some embodiments, the mutation in the kinase domain is in the kinase domain of a TrkB protein, and corresponds to a TrkA G595R or G667C mutation. In some embodiments, the mutation in the kinase domain is in the kinase domain of a TrkC protein, and corresponds to a TrkC G595R or G667C mutation. The amino acid sequences of human TrkA, TrkB, and TrkC are available from a variety of suitable databases (e.g., UniprotKB database or GenBank) and any suitable alignment program to align the kinase domains of TrkA, TrkB, and TrkC can be utilized (e.g., BLAST, the MUSCLE tool, etc.). In some embodiments, the NET with primary resistance to an agent that inhibits a Trk protein is administered a second agent that inhibits a Trk protein, wherein the NET does not have resistance to the second agent. In some embodiments, the NET with acquired resistance to an agent that inhibits a Trk protein is administered a second agent that inhibits a Trk protein, wherein the NET does not have resistance to the second agent.

In some embodiments, the method further comprises administering an additional therapy to the individual, wherein the additional therapy comprises administering a PI3K/Akt/mTOR pathway inhibitor, a TGF-β pathway inhibitor, a cell cycle inhibitor, a somatostatin analogue, an interferon, or an angiogenesis inhibitor. In some embodiments, the interferon is a type I interferon. In some embodiments, the type I interferon is IFN-α.

In some embodiments, the somatostatin analogue is octreotide, octreotate, pasireotide, or lanreotide. In some embodiments, the somatostatin analogue is radiolabeled. In some embodiments, the radiolabeled somatostatin analogue is [DOTA$^0$,Tyr$^3$]octreotate (Lutathera). In some embodiments, the additional therapy is everolimus (mTor inhibitor) temsirolimus (mTor inhibitor), bevacizumab (VEGF/angiogenesis inhibitor), sunitinib, or sorafenib (VEGF/MAPK inhibitor). In some embodiments, the additional therapy comprises surgery, chemotherapy, or radiation therapy.

EXAMPLES

The following examples are illustrative and non-limiting to the scope of the formulations and methods described herein.

Example 1—Treatment of a NET with the Trk Inhibitor Entrectinib

A 28 year-old previously healthy male patient presented with progressive low back pain and 11 kg weight loss over the previous year. He was a never-smoker, occasional alcohol drinker, and an avid runner. The patient had no relevant family history of cancer. The patient's laboratory analysis revealed elevated levels of alkaline phosphatase (406 U/liter; normal range 38-126 U/liter), with serum chromogranin A (29 ng/ml; normal range <95 ng/ml), 24 hour urine 5-hydroxyindoleacetic acid (5-HIAA) (7 mg/day; normal range 0-15 mg/day), and serotonin (117 ng/ml; normal range 50-200 ng/ml) all found to be normal.

A right upper quadrant ultrasound noted echogenic masses present in the liver. A computed tomography (CT) scan identified low-density liver lesions, adrenal masses, bulky retroperitoneal and pelvic lymphadenopathy, and diffuse bony disease. Lumbar magnetic resonance imaging (MRI) revealed a diffusely abnormal marrow signal, with expansion of multiple vertebral bodies producing epidural encroachment. $^{18}$F-fluorodeoxyglucose-positron-emission tomography (FDG-PET) imaging showed widespread FDG-uptake in the known areas of disease with the bulkiest and most intensely hypermetabolic disease corresponding to the bulky iliac lymphadenopathy, with a large left pelvic sidewall confluent mass (FIG. 1A). Multiple hypermetabolic liver lesions are seen, and innumerable lesions are seen throughout the skeleton (FIG. 1A). CT-guided biopsy of the left iliac bone reported well-differentiated neuroendocrine carcinoma (NETs), possibly from a lower GI source. Immunohistochemical (IHC) stains of the biopsied tissue revealed positive CD56, synaptophysin, chromogranin A, CK20, and villin staining, while TTF1, CDX-2, CK7, and CK19 were all found to be negative. Ki-67 IHC stain was observed in less than 3% of tumor cells and the specimen was observed to be without necrosis. Repeat CT-guided core biopsy of a right iliac soft tissue mass confirmed the absence of a high-grade component, consistent with the initial biopsy. An Indium-111 octreotide scan (octreoscan) revealed the widespread distribution of disease with increased scintigraphic activity localizing to bones, liver, and bulky retroperitoneum and pelvic adenopathy (FIG. 2A).

The patient received 3000 cGy of palliative radiotherapy to L1-S3 in 10 fractions for pain management followed by temozolomide and capecitabine chemotherapy. However, after three cycles of chemotherapy, the patient exhibited progressive disease with an axial contrast-enhanced abdominal CT scan showing bulky left pelvic sidewall and presacral masses (FIG. 3A).

Following chemotherapy, a tumor biopsy was obtained from the patient's lymph node, FFPE slides were prepared, and the NTRK status of the patient's NET was first analyzed by immunohistochemistry (IHC). The patient's tumor was positive for altered NTRK protein expression and the NET was subsequently analyzed by RNAseq NGS. An ETV6:NTRK3 translocation was identified in the patient's tumor and therapy was initiated with the investigational agent entrectinib, a potent oral tyrosine kinase inhibitor of TrkA, TrkB, and TrkC. After cycle #1 (one month) of entrectinib treatment, the patient exhibited a 6 kg weight gain and reported significant improvement in pain and energy levels. An axial contrast-enhanced abdominal CT scan (FIG. 3B) revealed a dramatic change in appearance of the left pelvic sidewall masses, which appeared swollen and measured larger, but was lower in density than the previous scan.

Figure 1B:
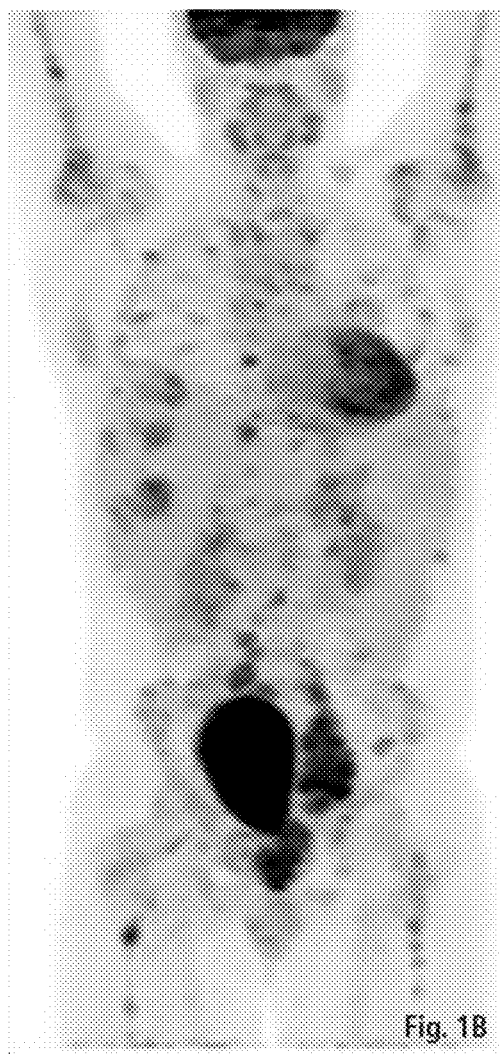
Figure 2A:
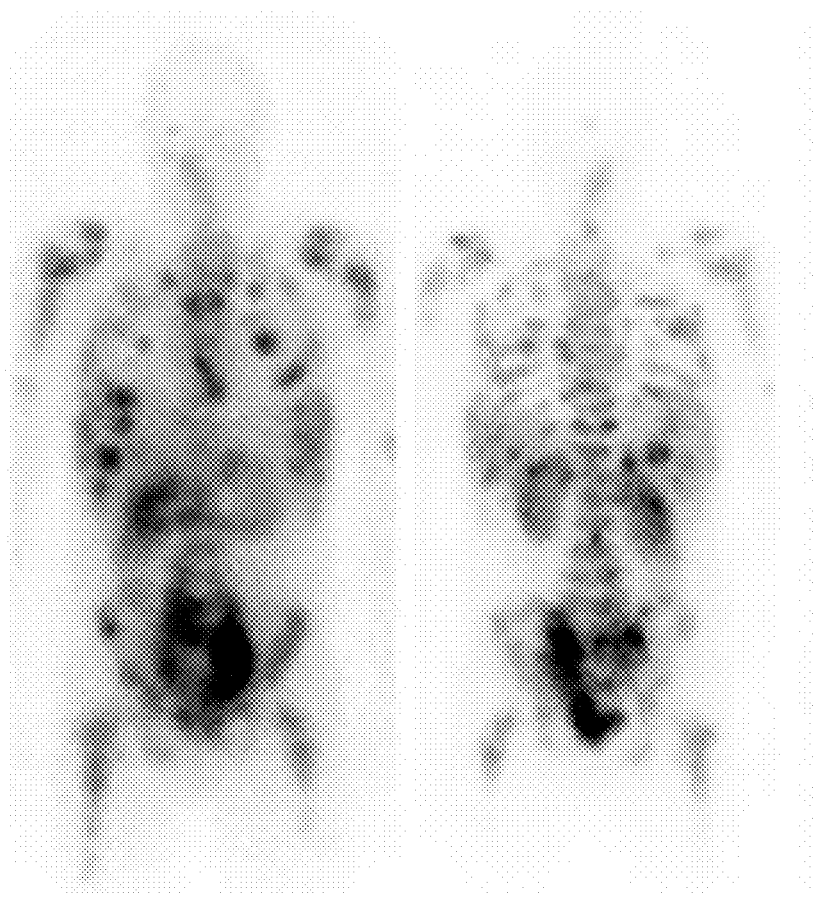
FIGS. 2A-B exemplify octreoscan imaging of a patient.
Figure 2B:
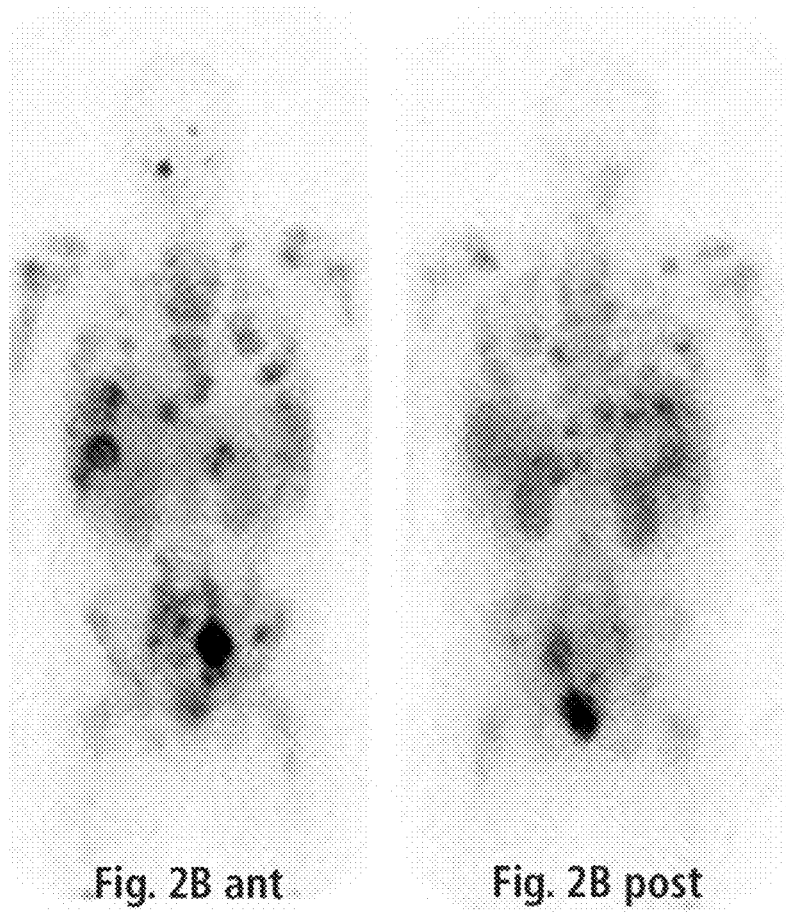

After 2 cycles of entrectinib treatment, FDG-PET-CT imaging demonstrated a larger pelvic and presacral adenopathy, but with tumor necrosis and decreased FDG-uptake compared to the earlier scans (FIGS. 1B and 2B; compare to FIGS. 1A and 2A). A clear improvement was observed in the skeleton following 2 cycles of entrectinib treatment (FIG. 1B, compare right proximal femur with femur in FIG. 1A). Follow-up CT scans in the subsequent months demonstrated continued shrinkage of the pelvic nodal masses. After 6 months of entrectinib treatment, an octreoscan confirmed significant reduction in overall disease burden, with reduced, but persistent activity in the liver, bones, and pelvic masses (FIG. 2B). While the bulkiest disease sites in the pelvis and the skeleton have shown clear improvement, some liver metastases have responded, while others have not. Clinically, the patient continues on entrectinib at 8 months with a stabilized 12 kg weight gain, normalized energy and activity, and markedly reduced pain control requirements. There were no notable adverse events.

Example 2—Identification of NTRK Fusion Genes in NETs Using an Illumina® Next-Generation Sequencing (NGS) Platform Tumor biopsies are taken from a patient having, or suspected of having, a NET. Formalin-fixed paraffin embedded (FFPE) tumor samples are prepared and tested using immunohistochemistry to identify patients potentially having an NTRK gene fusion or translocation. Patients with tumor samples indicating elevated levels of NTRK protein expression are then further tested by next-generation sequencing for confirmation and more detailed analysis of the NTRK genes.

The Archer® FusionPlex® NTRK Panel is a targeted sequencing assay that detects and identifies NTRK1, NTRK2, and NTRK3 fusions without prior knowledge of fusion partners or breakpoints. FusionPlex® panels utilize Anchored Multiplex PCR (AMP™) to generate target-enriched libraries for NGS. Designed for low nucleic acid input, AMP utilizes unidirectional gene-specific primers (GSPs) that enrich for both known and unknown mutations. The Archer® FusionPlex® NTRK Panel is designed to identify fusions including NTRK1 exons 8 and 10-13 (GenBank Accession: NM_002529); NTRK2 exons 11-17 (GenBank Accession: NM_006180); and NTRK3 exons 13-16 (GenBank Accession: NM_002530 and NM_001007156).

TNA (total nucleic acid, i.e., including both DNA and RNA) is extracted from the FFPE sample using Agencourt FormaPure (Cat. # A33342) extraction kit according to manufacturer's instructions but with the modifications set forth in the Archer® FusionPlex® NTRK Protocol for Illumina®. Alternatively, RNA can be extracted from a fresh, non-FFPE tumor biopsy sample.

Using the Archer® FusionPlex® NTRK Kit for Illumina® (SK0031-ILMN), cDNA is generated from the RNA or TNA extracted from biopsied tumors:

Step 1: 2-250 ng of extracted TNA or 20-250 ng of RNA is hybridized with random primers.

Step 2: A first strand of cDNA is synthesized for each sample.

Step 3: Using the first strand of cDNA, a second strand of cDNA is synthesized for each sample.

Step 4: qPCR is carried out on the cDNA samples as a quality control step to determine the quality of the cDNA starting material (QC can also be run after first strand synthesis in parallel with second strand generation).

Step 5: End repair/dA-Tailing of the cDNA is carried out.

Step 6: After end repair, the reaction mixture is purified using an AMPure XP Beads Purification kit and MBC Adapters are then ligated onto the cDNA.

Step 7: After ligation, the reaction in cleaned up with AMPure bead purification and a first PCR with NTRK GSPs (GSP1; #SA0103) is carried out.

Step 8: The reaction is then cleaned up and a second PCR is carried out with NTRK GSPs (GSP2; #SA0104) according to manufacturer's instructions. After the second PCR the PCR reaction mixture is purified using AMPure beads.

Step 9: Library quantification is performed using the KAPA Biosystems qPCR kit (Cat. # KK4824) to quantify the concentration of the library, assuming a 200 bp fragment length. After quantification, barcoded libraries are pooled at equimolar concentrations and are sequenced on an Illumina MiSeq or NextSeq sequencing platform according to manufacturer instructions.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating a gastrointestinal neuroendocrine tumor (NET) in an individual in need thereof, comprising administering to the individual a therapeutically effective amount of an agent that inhibits a tropomyosin receptor kinase (Trk) protein, wherein the NET is associated with a Trk fusion protein comprising:
   (a) an N-terminal polypeptide region comprising a sequence from a polypeptide other than a TrkA, TrkB, or TrkC polypeptide; and
   (b) a C-terminal polypeptide region comprising a sequence from a TrkA, TrkB, or TrkC polypeptide, wherein the TrkA, TrkB, or TrkC polypeptide comprises a TrkA, TrkB, or TrkC tyrosine kinase signaling domain comprising TrkA, TrkB, or TrkC kinase activity.

2. The method of claim 1, wherein the Trk fusion protein is derived from an NTRK gene fusion, wherein the NTRK gene fusion comprises an NTRK1, NTRK2, or NTRK3 tyrosine kinase signaling domain.

3. The method of claim 1, wherein the Trk fusion protein is constitutively active.

4. The method of claim 1, wherein the Trk fusion protein comprises:
   (a) an N-terminal polypeptide region comprising a sequence of a MPRIP, CD74, RABGAP1L, TPM3, TPR, TFG, PPL, CHTOP, ARHGEF2, NFASC, BCAN, LMNA, TP53, QKI, NACC2, VCL, AGBL4, TRIM24, PAN3, AFAP1, SQSTM1, ETV6, BTBD1, LYN, RBPMS, RFWD2, IRF2BP2, SSBP2, C18ORF8, RNF213, TBC1, DNER, PLEKHA6, PEAR1, MRPL24, MDM4, GRIPAP1, EPS15, DYNC2H1, CEL, EPHB2, EML4, HOMER2, TEL, or FAT1 polypeptide; and
   (b) a C-terminal polypeptide region comprising a sequence of a TrkA, TrkB, or TrkC polypeptide, wherein the TrkA, TrkB, or TrkC polypeptide comprises a TrkA, TrkB, or TrkC tyrosine kinase signaling domain comprising TrkA, TrkB, or TrkC kinase activity.

5. The method of claim 4, wherein the N-terminal polypeptide region comprises a sequence from an ETV6 polypeptide.

6. The method of claim 5, wherein the C-terminal polypeptide region comprises a sequence from a TrkC polypeptide.

7. The method of claim 1, wherein the Trk fusion protein comprises:
   (a) an N-terminal polypeptide region comprising a sequence from a polypeptide other than a TrkA, TrkB, or TrkC polypeptide; and
   (b) a C-terminal polypeptide region comprising a sequence from a TrkA polypeptide, wherein the TrkA polypeptide comprises a TrkA tyrosine kinase signaling domain comprising TrkA kinase activity; and
   wherein the Trk fusion protein is a TP53-TrkA, LMNA-TrkA, CD74-TrkA, TFG-TrkA, TPM3-TrkA, NFASC-TrkA, BCAN-TrkA, MPRIP-TrkA, TPR-TrkA, RFWD2-TrkA, IRF2BP2-TrkA, SQSTM1-TrkA, SSBP2-TrkA, RABGAP1L-TrkA, C18ORF8-TrkA, RNF213-TrkA, TBC1D22A-TrkA, C200RF112-TrkA, DNER-TrkA, ARHGEF2-TrkA, CHTOP-TrkA, PPL-TrkA, PLEKHA6-TrkA, PEAR1-TrkA, MRPL24-TrkA, MDM4-TrkA, LRRC71-TrkA, GRIPAP1-TrkA, EPS15-TrkA, DYNC2H1-TrkA, CEL-TrkA, EPHB2-TrkA, or TGF-TrkA fusion protein.

8. The method of claim 1, wherein the Trk fusion protein comprises:
   (a) an N-terminal polypeptide region comprising a sequence from a polypeptide other than a TrkA, TrkB, or TrkC polypeptide; and
   (b) a C-terminal polypeptide region comprising a sequence from a TrkB polypeptide, wherein the TrkB polypeptide comprises a TrkB tyrosine kinase signaling domain comprising TrkB kinase activity;
   wherein the fusion protein is a NACC2-TrkB, QKI-TrkB, AFAP1-TrkB, PAN3-TrkB, SQSTM1-TrkB, TRIM24-TrkB, VCL-TrkB, AGBL4-TrkB, or DAB2IP-TrkB fusion protein.

9. The method of claim 1, wherein the Trk fusion protein comprises:
   (a) an N-terminal polypeptide region comprising a sequence from a polypeptide other than a TrkA, TrkB, or TrkC polypeptide; and
   (b) a C-terminal polypeptide region comprising a sequence from a TrkC polypeptide, wherein the TrkC polypeptide comprises a TrkC tyrosine kinase signaling domain comprising TrkC kinase activity;
   wherein the Trk fusion protein is a ETV6-TrkC, BTBD1-TrkC, LYN-TrkC, RBPMS-TrkC, EML4-TrkC, HOMER2-TrkC, TFG-TrkC, FAT1-TrkC, or TEL-TrkC fusion protein.

10. The method of claim 1, wherein the agent that inhibits a Trk protein is a kinase inhibitor.

11. The method of claim 1, wherein the agent that inhibits a Trk protein is entrectinib, RXDX-102, altiratinib, larotrectinib, LOXO-195, sitravatinib, cabozantinib, merestinib, dovitinib, crizotinib, TSR-011, DS-6051, PLX7486, lestaurtinib, danusertib, F17752, AZD6918, AZD7451, or AZ-23, or a pharmaceutically acceptable salt thereof.

12. The method of claim 11, wherein the agent is entrectinib, or a pharmaceutically acceptable salt thereof.

13. The method of claim 1, wherein the gastrointestinal NET is a small intestine, large intestine, pancreatic, appendix, gastric, or rectal NET.

14. The method of claim 1, wherein the gastrointestinal NET has metastasized to a secondary tissue.

15. The method of claim 14, wherein the secondary tissue is a lymph node, mesentery, liver, bone, lung, or brain.

16. A method of treating a gastrointestinal neuroendocrine tumor (NET) in an individual in need thereof comprising: (a) providing a sample of NET genetic material from the individual; (b) determining whether the sample of NET genetic material comprises a NTRK gene fusion comprising a C-terminal region comprising a NTRK1, NTRK2, or NTRK3 tyrosine kinase signaling domain; and (c) administering to the individual a therapeutically effective amount of an agent that inhibits a tropomyosin receptor kinase (Trk) protein.

17. The method of claim 16, wherein the sample of NET genetic material is total nucleic acid obtained from formalin-fixed paraffin-embedded (FFPE) tumor biopsy sample.

18. The method of claim 16, further comprising sequencing the sample of NET genetic material to determine whether the sample of NET genetic material comprises the NTRK gene fusion.

19. The method of claim 16, further comprising amplifying the sample of NET genetic material using NTRK1, NTRK2, or NTRK3-specific primers prior to determining whether the sample of NET genetic material comprises the NTRK gene fusion.

* * * * *